(12) United States Patent
Lai et al.

(10) Patent No.: US 11,701,501 B2
(45) Date of Patent: Jul. 18, 2023

(54) FLUID PRESSURE GUN DEVICE FOR BALLOON CATHETER

(71) Applicant: Ming-Hsiao Lai, Dacun Township, Changhua County (TW)

(72) Inventors: Ming-Hsiao Lai, Dacun Township, Changhua County (TW); Kuo-Shu Huang, Changhua (TW)

(73) Assignee: Ming-Hsiao Lai, Dacun Township (TW)

( * ) Notice: Subject to any disclaimer, the term of this patent is extended or adjusted under 35 U.S.C. 154(b) by 411 days.

(21) Appl. No.: 17/151,997

(22) Filed: Jan. 19, 2021

(65) Prior Publication Data

US 2022/0226621 A1  Jul. 21, 2022

(51) Int. Cl.
*A61M 25/10* (2013.01)

(52) U.S. Cl.
CPC ...... *A61M 25/10182* (2013.11); *A61M 25/10* (2013.01); *A61M 25/104* (2013.01); *A61M 25/1018* (2013.01); *A61M 25/10184* (2013.11); *A61M 25/10187* (2013.11); *A61M 25/10188* (2013.11); *A61M 2205/3331* (2013.01)

(58) Field of Classification Search
CPC ........................................... A61M 2205/3331
See application file for complete search history.

(56) References Cited

U.S. PATENT DOCUMENTS

| | | | | |
|---|---|---|---|---|
| 5,019,041 A | * | 5/1991 | Robinson | A61M 25/10184 604/920 |
| 5,168,757 A | * | 12/1992 | Rabenau | A61M 25/104 604/920 |
| 5,306,248 A | * | 4/1994 | Barrington | A61M 25/104 604/920 |
| 5,318,534 A | * | 6/1994 | Williams | A61M 25/104 604/920 |
| 6,106,496 A | * | 8/2000 | Arnissolle | A61M 25/10182 604/207 |
| 2010/0116360 A1 | * | 5/2010 | Kanner | A61M 25/10182 137/383 |
| 2013/0261601 A1 | * | 10/2013 | Webler | A61M 25/10182 604/509 |
| 2016/0058988 A1 | * | 3/2016 | Kesten | A61M 25/0097 604/97.02 |
| 2017/0246433 A1 | * | 8/2017 | Kanner | A61M 25/10182 |
| 2020/0376240 A1 | * | 12/2020 | Jin | A61M 29/02 |
| 2022/0193380 A1 | * | 6/2022 | Collins | A61M 5/31505 |

* cited by examiner

*Primary Examiner* — Nathan R Price
*Assistant Examiner* — Anh Bui
(74) *Attorney, Agent, or Firm* — Egbert, McDaniel & Swartz, PLLC

(57) ABSTRACT

A fluid pressure gun device for a balloon catheter includes a tubular cavity, a fluid tube, a pressure monitoring device, a plunger, a screw structure, a cover and a detent structure, wherein inside the body of the cavity forms a chamber. The plunger is disposed in the chamber, and the inside of the casing forms a chamber. The screwing structure includes two screwing blocks, and each screwing block is oppositely arranged in the chamber according to the plunger as the center. Each of the screw blocks is screwed with the plunger, and a plurality of springs respectively lean against the screw block and the cover. The detent structure is used to depart the screw blocks from the plunger. The plunger is supported by each screw block at least on two opposite sides, and making it a highly reliable combination of the plunger and each screw block.

18 Claims, 11 Drawing Sheets

FLUID PRESSURE GUN DEVICE FOR BALLOON CATHETER

CROSS-REFERENCE TO RELATED U.S. APPLICATIONS

Not applicable.

BACKGROUND OF THE INVENTION

1. Field of the Invention

The present invention relates generally to a pressure unit for balloon catheter, and more particularly to an innovative structure type of a fluid pressure gun device for a balloon catheter.

2. Description of Related Art Including Information Disclosed Under 37 CFR 1.97 and 37 CFR 1.98.

The balloon catheter is a soft catheter provided with an inflatable balloon at the top. In the angioplasty, the balloon catheter is usually used in blood vessels to widen narrow regions or make channels. When in use, the uninflated balloon is positioned, the balloon is inflated according to different surgical purposes, the balloon expands and pushes blood vessels open, the balloon catheter can be removed after the balloon is deflated.

It is known that a fluid injection device is used to inflate and deflate the balloon for the angioplasty inside the blood vessel, including a tubular main body, the front end of the main body is connected to a fluid tube, a chamber is formed inside the main body, the chamber communicates with the fluid tube, the fluid tube communicates with the balloon catheter through a connection fitting. The front end of the main body is provided with a pressure monitoring device for monitoring and indicating the pressure inside the chamber. A plunger is movably disposed in the chamber, the front end of the plunger is provided with a piston, the back end of the plunger extends out of the main body and has an operating part, the operating part is operated to make the plunger pull the piston to reciprocate inside the chamber, so as to inject fluid into or extract fluid from the balloon. A male thread is formed on the periphery of the plunger. One side of the plunger of the main body is provided with a screw structure, the screw structure has a female thread fitting the male thread, the screw structure can be optionally combined with or disengaged from the plunger by laterally pushing or pulling the screw structure.

In the initial stage when the balloon is injected with fluid to dilate the balloon, the screw structure is disengaged from the plunger, and the plunger and the piston can be moved forward rapidly. When the screw structure is laterally combined with the plunger, the plunger and the piston can push the fluid into the balloon while the shot volume is controlled accurately by turning the plunger. To make the fluid depart from the balloon to deflate the balloon, the screw structure is laterally disengaged from the plunger, the pressure of the balloon and the fluid pushes the piston, so that the piston and the plunger can move backward rapidly, the balloon is deflated rapidly.

The screw structure is combined with the plunger, the plunger can resist the pressure from the fluid, but the screw structure is only combined with the plunger on one side of the plunger, the plunger is partially stressed, said pressure may induce slight lateral deformation of the plunger in the direction far from the screw structure, the reliability of effective screwing of the female thread and the male thread is influenced. The female thread and the male thread have the risk of structural failure, and the plunger may be disengaged from the screw structure.

BRIEF SUMMARY OF THE INVENTION

The primary objective of the present invention is to provide a fluid pressure gun device for a balloon catheter.

Based on said objective, the technical characteristic of problem solving of the present invention is that the fluid pressure gun device for a balloon catheter includes a tubular cavity, a fluid tube, a pressure monitoring device, a plunger, a screw structure, a cover casing and a detent structure. A chamber is formed inside the cavity for storing fluid, and the front end of said cavity is connected to said fluid tube, Said chamber communicates with said fluid tube. Said fluid tube is provided with a connection fitting, so that the fluid tube communicates with a balloon catheter. Said pressure monitoring device is disposed in the cavity for monitoring and indicating the pressure of the fluid. Said plunger is movably disposed in said chamber. A piston is pivoted at the front end of said plunger, and said piston and said cavity are fitted closely, so that said plunger pulls the piston to reciprocate in said chamber to inject the fluid into or extract the fluid from the balloon of said balloon catheter. An operating part is formed at the back end of said plunger, facilitating the axial displacement or rotation of said plunger. Said screw structure is optionally combined with or disengaged from said plunger, so that said plunger resists the pressure from the fluid, and the displacement of said plunger and said piston is controlled.

Said cover casing is arranged at the back end of the cavity. A chamber is formed inside the cover casing. Said plunger protrudes out of the back end of the cover casing through said chamber, and said plunger is provided with a first screw thread structure. Said first screw thread structure is at least formed on opposite side of said plunger.

Said screw structure is disposed in said chamber. Said screw structure comprises two screw blocks, said screw blocks being oppositely arranged centering on said plunger said screw blocks form a second screw thread structure fitting sad first screw thread structure respectively, so that said screw blocks are screwed on said plunger. Said screw structure has several springs between said screw blocks and said cover casing. Said springs prop said screw block and said cover casing respectively, so as to provide thrust. The screwing reliability of said screw blocks and said plunger is enhanced.

Said detent structure comprises two cams, two arm levers and one connecting rod, wherein said cam is an elliptical disc, said cams are pivoted between said screw blocks respectively, and said cams are adjacent to both ends of said screw blocks far from said plunger respectively. A construction line is defined to pass through the center of said cams, and the construction line radially passes through said plunger. Said arm levers are connected to said cams respectively. Both ends of said connecting rod are connected to said arm levers respectively, so that said arm levers pull said cams to rotate synchronously to perform combination or disengagement of said second screw thread structure and said first screw thread structure.

In terms of the main effect and advantage of the present invention, the plunger is supported by the screw blocks at least on two opposite sides, the first screw thread structure and the second screw thread structure have high reliability of effective screwing.

Another purpose of the present invention is to achieve the advantage and practical progressiveness of easy combination or disengagement of the screw blocks and the plunger based on the detent structure.

DETAILED DESCRIPTION OF THE INVENTION

Figure 1:
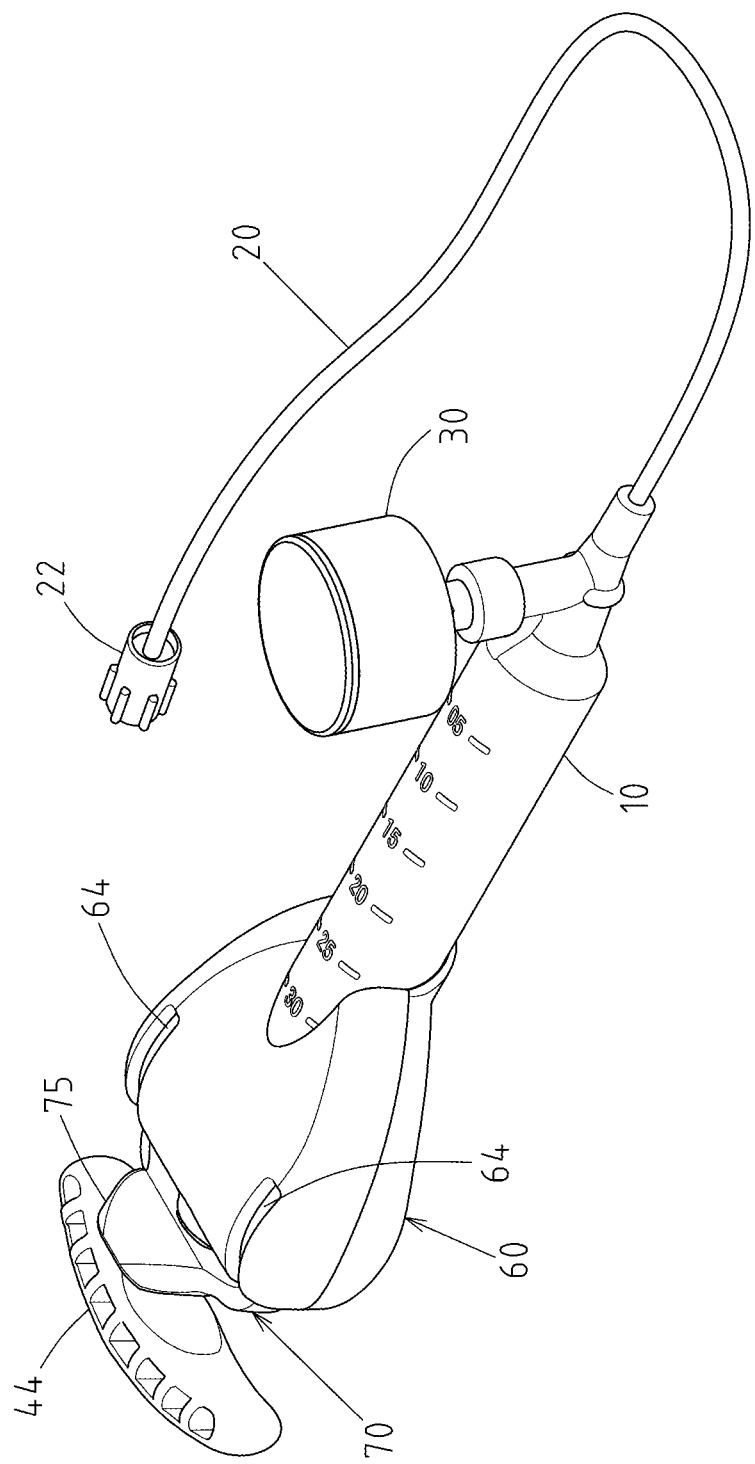
FIG. 1 is a stereogram (1) of the preferred embodiment of the present invention.
Figure 2:
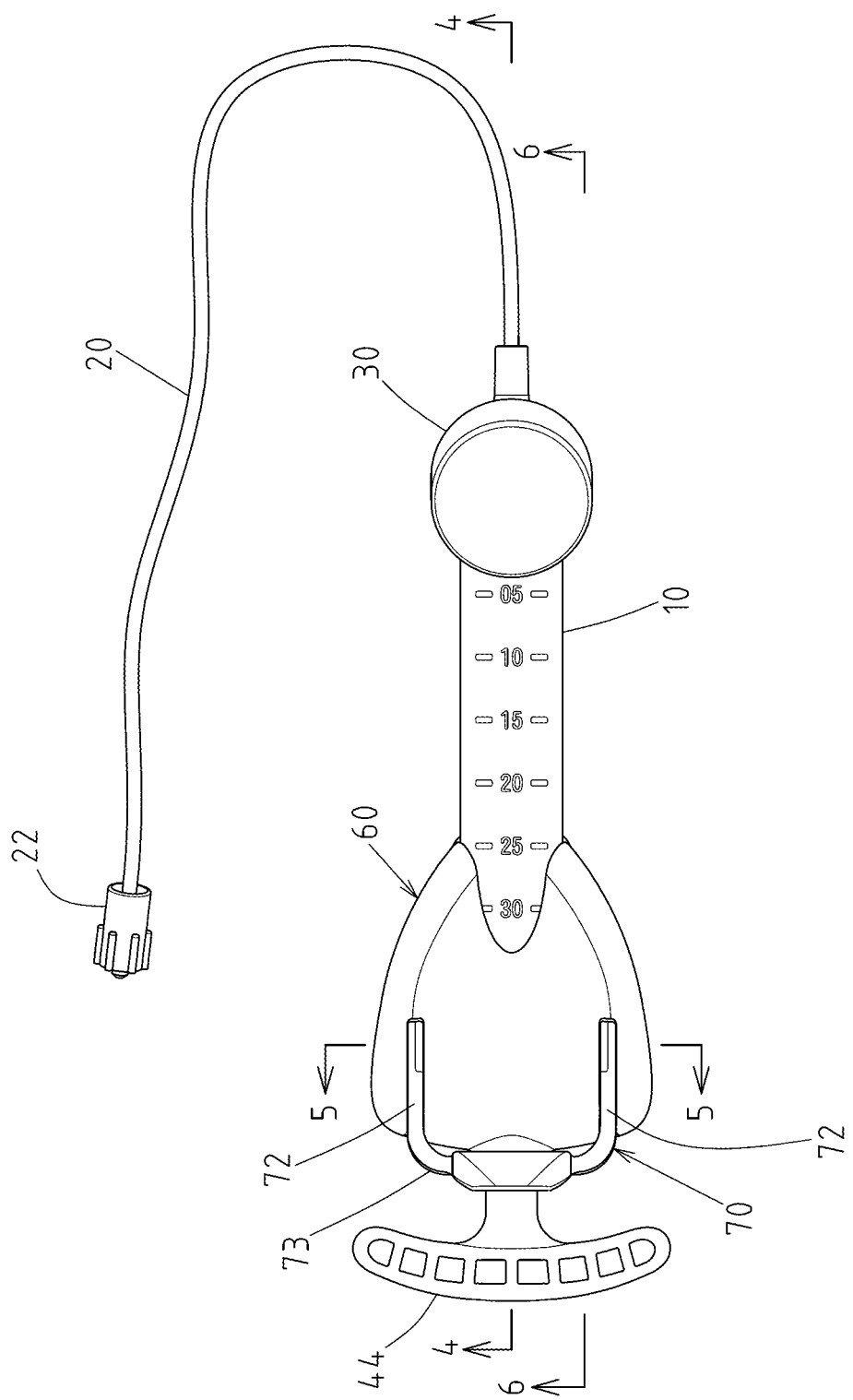
FIG. 2 is a top view of the preferred embodiment of the present invention in the state shown in FIG. 1.
Figure 3:
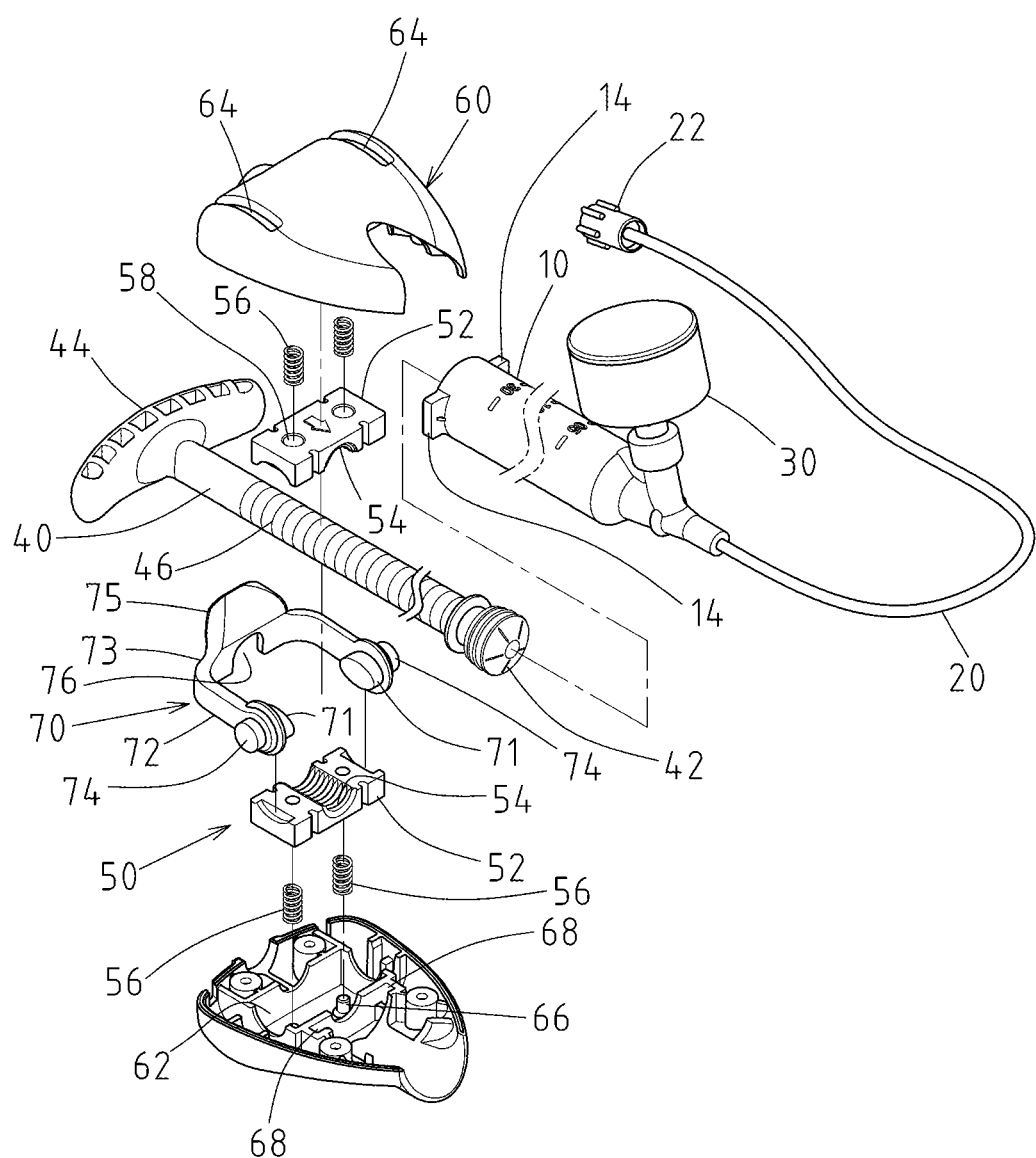
FIG. 3 is a three-dimensional exploded diagram of the preferred embodiment of the present invention.
Figure 4:
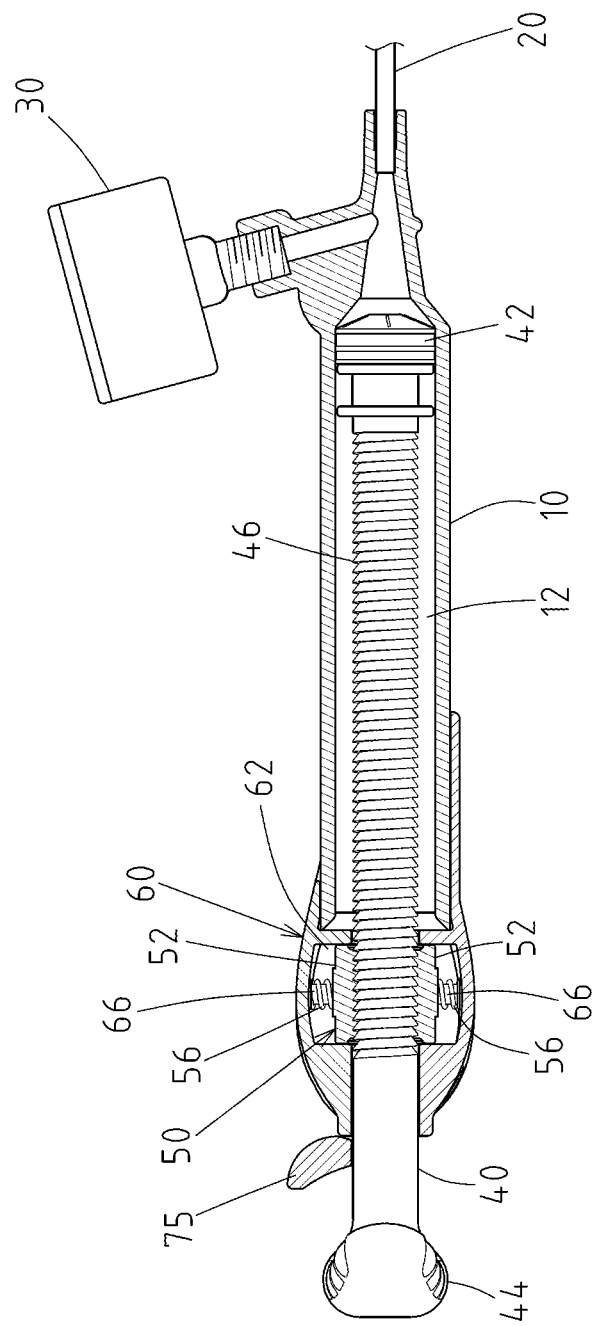
FIG. 4 is the 4-4 section view of FIG. 2.

As shown in FIG. 1 to FIG. 11, the preferred embodiment of said fluid pressure gun device for balloon catheter includes a tubular cavity 10, a fluid tube 20, a pressure monitoring device 30, a plunger 40, a screw structure 50, a cover casing 60 and a detent structure 70. Wherein a chamber 12 is formed inside the cavity 10 for storing fluid (not shown in the figure), the fluid can be gas or liquid. The front end of the cavity 10 is connected to the fluid tube 20. The chamber 12 communicates with the fluid tube 20. The fluid tube 20 is provided with a connection fitting 22, so that the fluid tube 20 communicates with a balloon catheter (not shown in the figure). The pressure monitoring device 30 is disposed in the cavity 10 for monitoring and indicating the pressure of the fluid. The plunger 40 is movably disposed in the chamber 12. A piston 42 is axially pivoted at the front end of the plunger 40, the piston 42 and the cavity 10 are fitted closely, so that the plunger 40 pulls the piston 42 to reciprocate in the chamber 12 to inject the fluid into or extract the fluid from the balloon of the balloon catheter, and to prevent the fluid from leaking between the piston 42 and the cavity 10. An operating part 44 is formed at the back end of the plunger 40, facilitating the rotation or axial displacement of the plunger 40. The screw structure 50 is optionally combined with or disengaged from the plunger 40, so that the plunger 40 resists the pressure from the fluid, and the displacement of the plunger 40 and the piston 42 is controlled. The plunger 40 is provided with a first screw thread structure 46, in this case, the first screw thread structure 46 is a saw-tooth thread, and the first screw thread structure 46 surrounds the lateral circumference of the plunger 40. In other embodiments, the first screw thread structure 46 can be formed on the opposite side of the plunger 40.

The cover casing 60 is arranged at the back end of the cavity 10. A chamber 62 is formed inside the cover casing 60. The plunger 40 protrudes out of the back end of the cover casing 60 through the chamber 62. The screw structure 50 is disposed in the chamber 62. The screw structure 50 comprises two screw blocks 52. The screw blocks 52 are oppositely arranged centering on the plunger 40. The screw blocks 52 form a second screw thread structure 54 fitting the first screw thread structure 46 respectively, so that the screw blocks 52 are screwed on the plunger 40. The screw structure 50 is provided with several springs 56 between the screw blocks 52 and the cover casing 60. The springs 56 prop the screw block 52 and the cover casing 60 respectively. The springs 56 push the screw block 52 respectively, increasing the screwing reliability of the screw blocks 52 and the plunger 40. The second screw thread structure 54 is formed in the central part of the side of the screw block 52 facing the plunger 40. The springs 56 prop the portions near two ends of the screw block 52 respectively, so that the screw block 52 is stressed evenly, the screwing reliability of the screw blocks 52 and the plunger 40 is further increased.

When the screw block 52 is screwed on the plunger 40, the plunger 40 can resist the pressure from the fluid. As the first screw thread structure 46 is at least formed on opposite side of the plunger 40, the plunger 40 is supported by the screw blocks 52 at least on two opposite sides, the plunger 40 is stressed evenly. Said pressure will not induce lateral deformation of the plunger 40. The first screw thread structure 46 and the second screw thread structure 54 have high reliability of effective screwing. Said pressure will not induce structural failure of the first screw thread structure 46 and the second screw thread structure 54.

Figure 5:
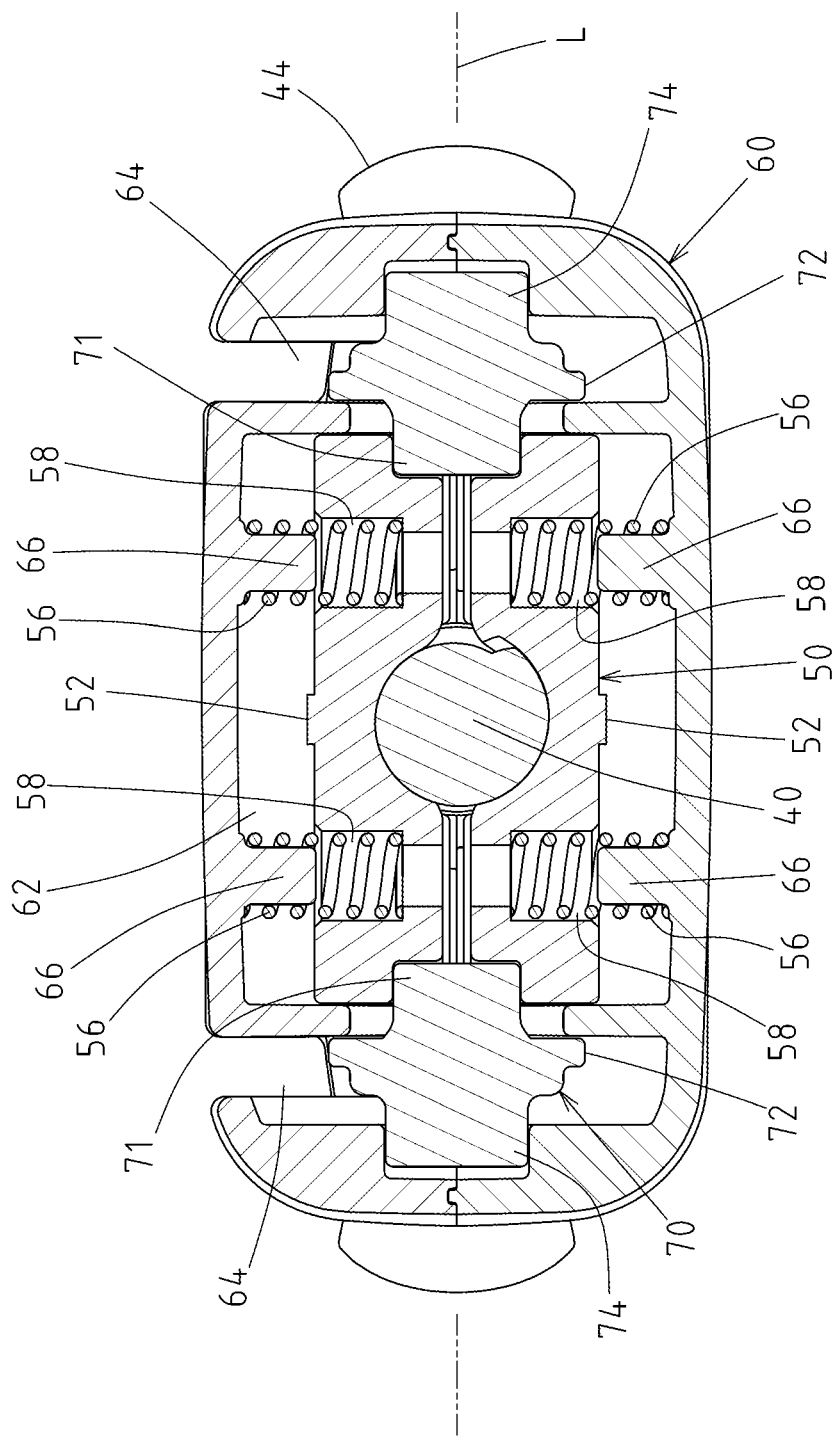
FIG. 5 is the 5-5 section view of FIG. 2, showing the screw structure and plunger bonding state.
Figure 6:
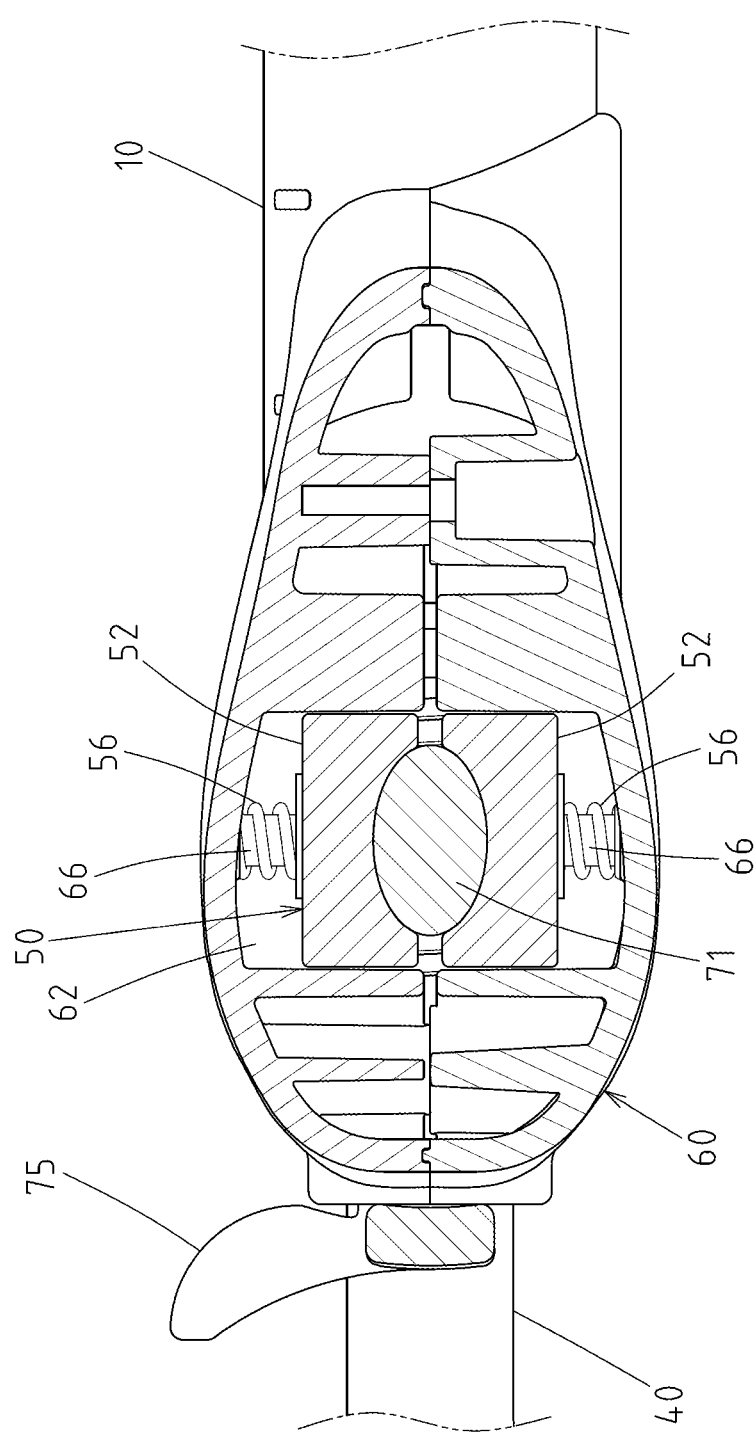
FIG. 6 is the 6-6 section view of FIG. 2, showing the state of cam pivoted between two screw blocks.
Figure 7:
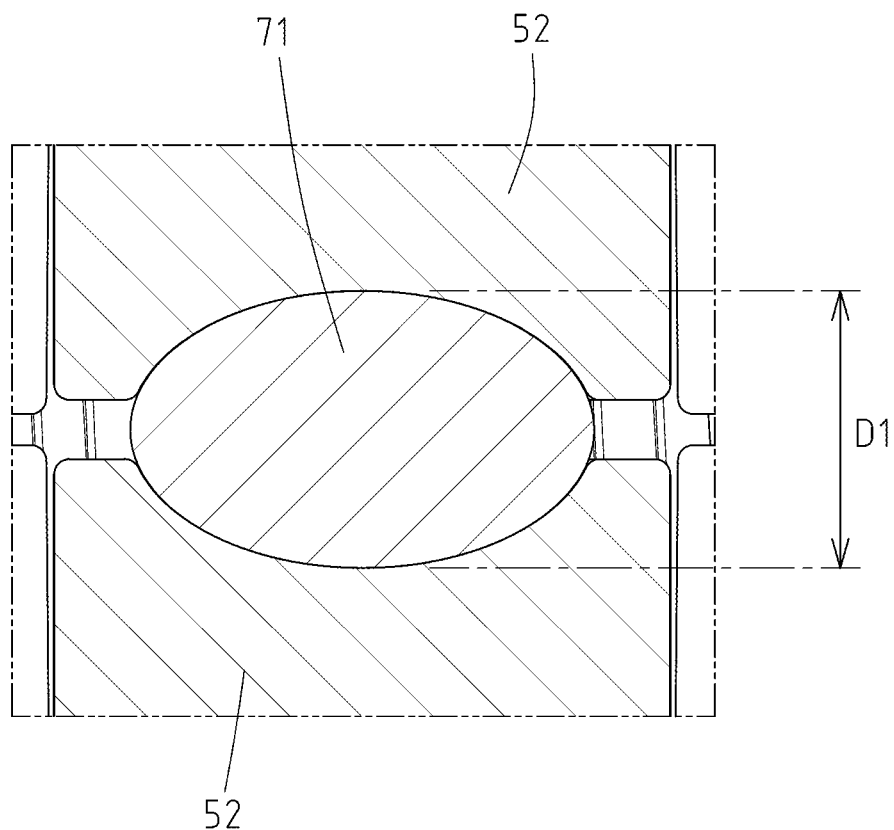
FIG. 7 is a drawing of partial enlargement of the cam and screw blocks in FIG. 6.
Figure 8:
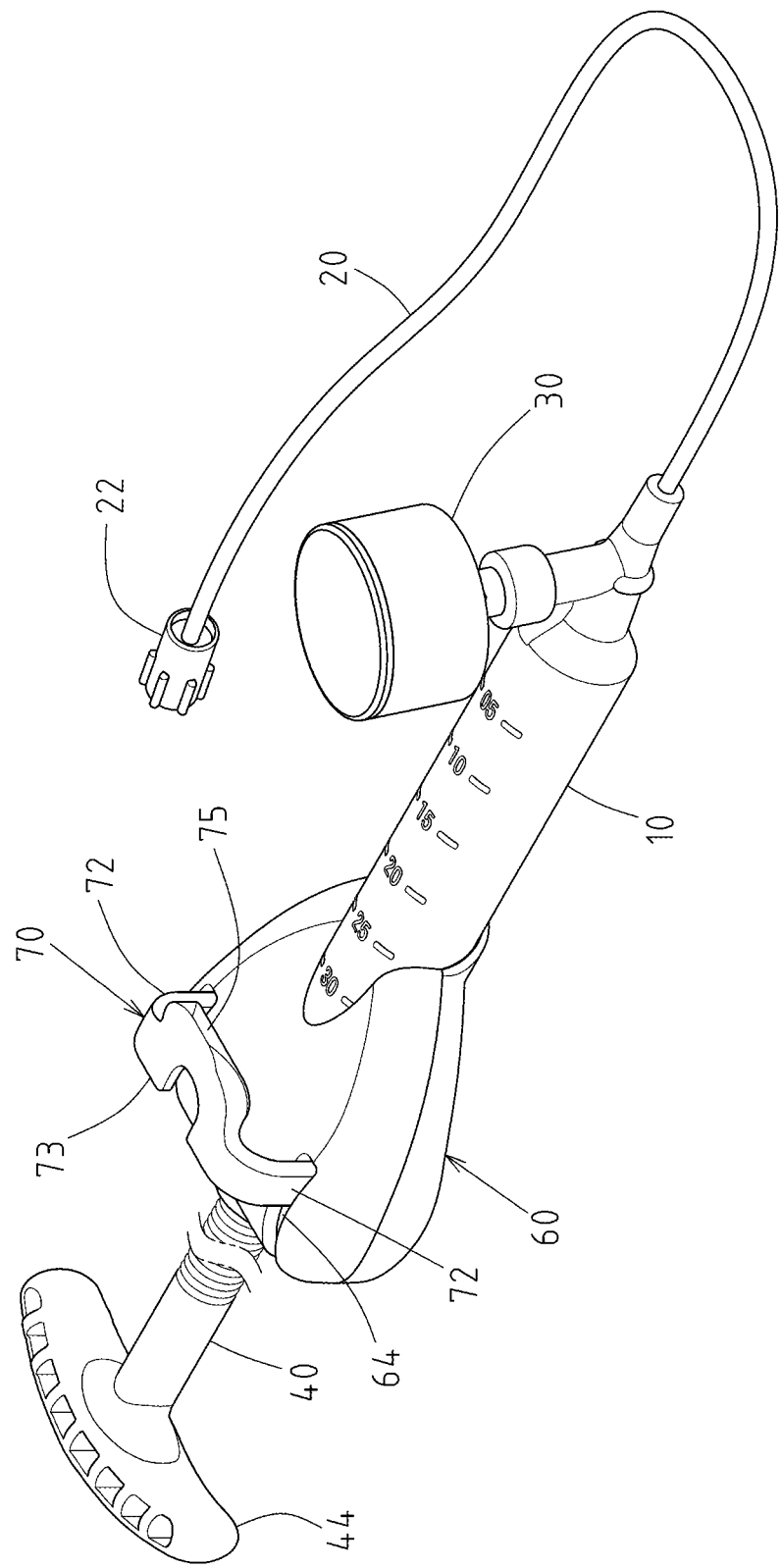
FIG. 8 is a stereogram (2) of the preferred embodiment of the present invention, showing the state of operating the detent structure to disengage the screw structure from the plunger.
Figure 9:
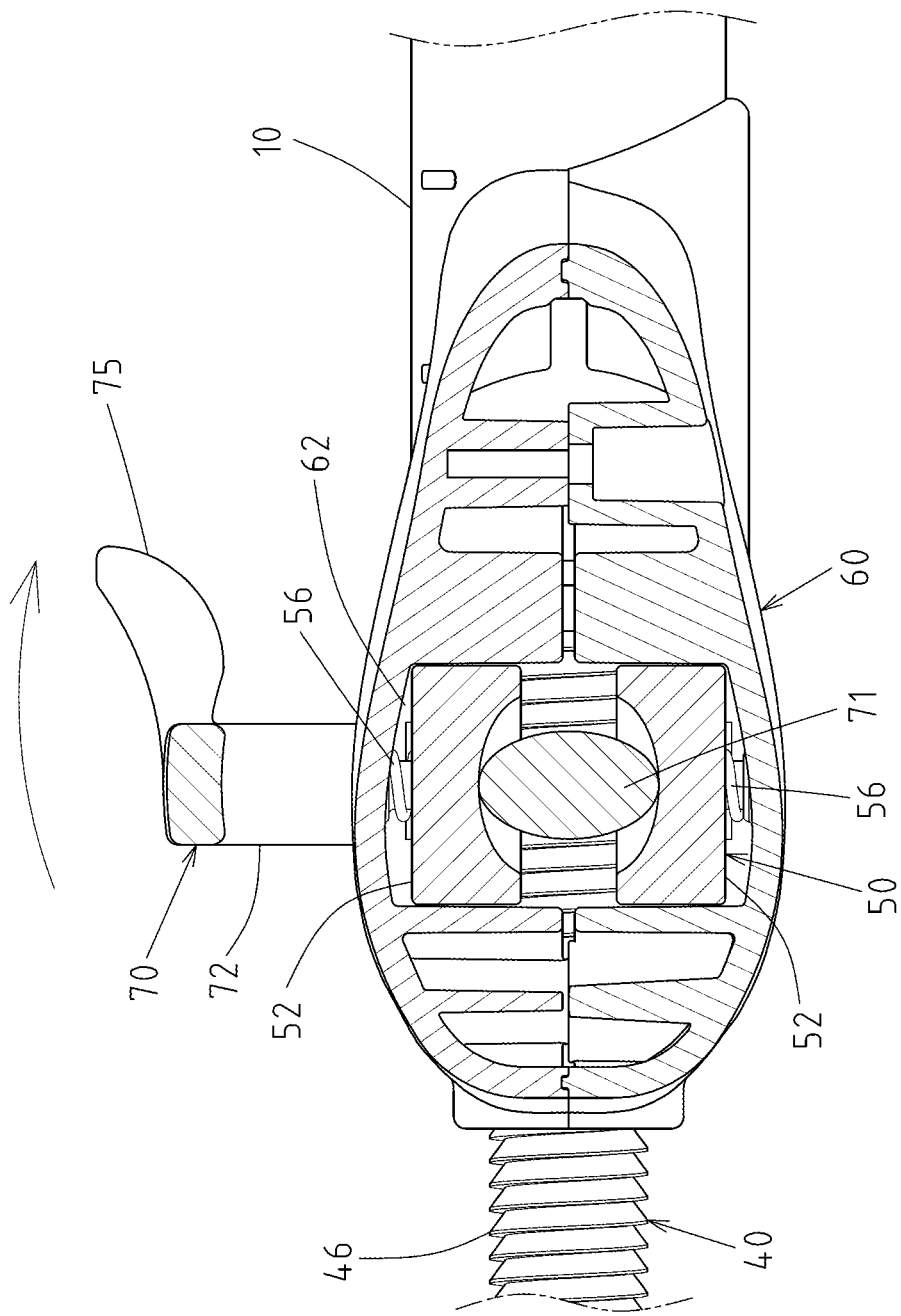
FIG. 9 is a partial section view of the detent structure and screw structure in the preferred embodiment of the present invention, showing the state of the cam disengaging the screw structure from the plunger.
Figure 10:
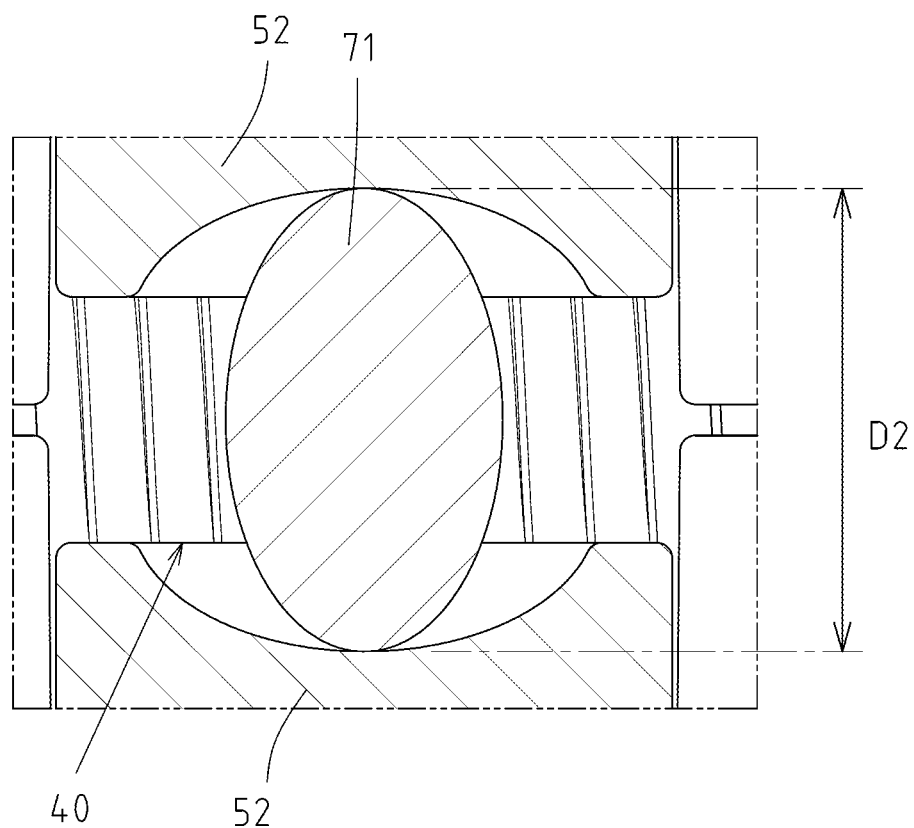
FIG. 10 is a drawing of partial enlargement of the cam and screw blocks in FIG. 9.
Figure 11:
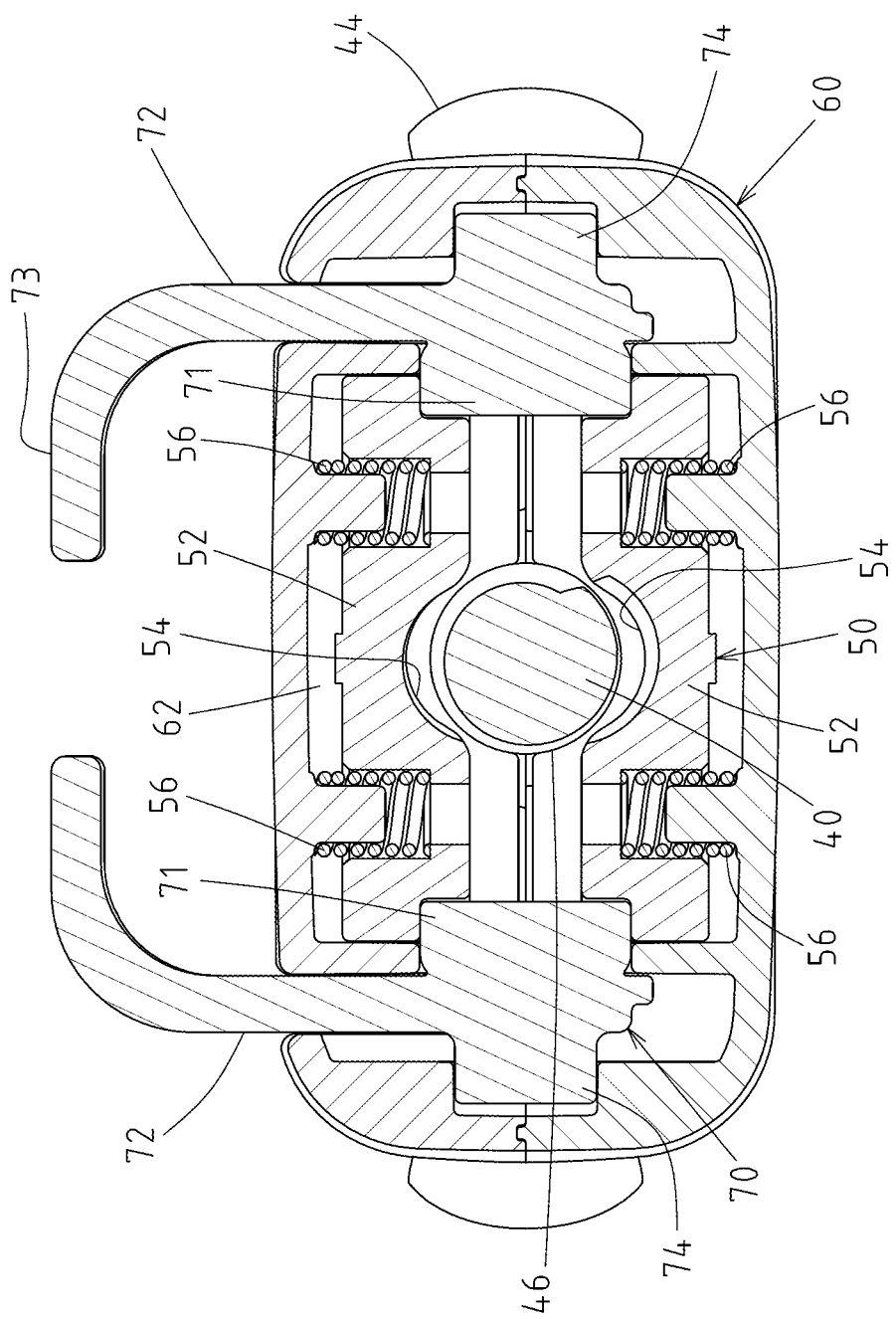
FIG. 11 is a partial section view of the plunger and screw structure in the preferred embodiment of the present invention, showing the disengaged state of the screw structure and plunger.

The detent structure 70 comprises two cams 71, two arm levers 72 and one connecting rod 73. Wherein the cam 71 is an elliptical disc, the cams 71 are pivoted between the screw blocks 52 respectively, and the cams 71 are adjacent to both ends of the screw blocks 52 far from the plunger 40 respectively. A construction line L is defined to pass through the center of the cams 71, the construction line L radially passes through the plunger 40. The arm levers 72 are connected to one side of the cams 71 respectively. Both ends of the connecting rod 73 are connected to the arm levers 72 respectively. When the connecting rod 73 is pulled, the arm levers 72 pull the cams 71 to rotate synchronously, as shown in FIG. 5 to FIG. 7. When both ends of short diameter D1 of the cam 71 point at the screw blocks 52, the spring 56 provides thrust to make the screw blocks 52 lean against the plunger 40 respectively, the second screw thread structure 54 engages with the first screw thread structure 46, as shown in FIG. 9 to FIG. 11. When both ends of long diameter D2 of the cam 71 point at the screw blocks 52, the cam 71 pushes the screw blocks 52 to move away from the plunger 40 respectively, the second screw thread structure 54 is disengaged from the first screw thread structure 46, the combination or disengagement of the screw blocks 52 and the plunger 40 is easy.

The screw blocks 52 are oppositely movable in the chamber 62, the chamber 62 localizes the screw blocks 52 and confines the path of actuation of the screw blocks 52 against the plunger 40, the reliability of combination or disengagement of the screw blocks 52 and the plunger 40 is enhanced, it is a better implementation option.

The cover casing 60 forms two through grooves 64, the arm levers 72 pass through the through grooves 64 respectively, so that the arm levers 72 extend into the cover casing 60 respectively. The arm levers 72 are provided with a pivot 74 respectively, the pivots 74 are coaxial with the cams 71 respectively. The pivots 74 are pivoted on the cover casing 60 respectively. When the connecting rod 73 is pulled, the arm levers 72 prime the cams 71 to rotate synchronously centering on the pivots 74 respectively.

The connecting rod 73 is adjacent to the rear edge of the cover casing 60, and a gripping part 75 is formed in the midsection of the connecting rod 73, the operator can grip the gripping part 75 and pull the connecting rod 73, the handiness of pulling the arm lever 72 is enhanced. The connecting rod 73 forms a notch 76 fitting the plunger 40, the plunger 40 passes through the notch 76. Hereby, when the screw structure 50 is combined with the plunger 40, the connecting rod 73 gets closer to the plunger 40.

The screw blocks 52 form several recess holes 58 respectively. Several convex pins 66 protrude from the cover casing 60. The springs 56 are pivoted in the recess holes 58 respectively, and the springs 56 are fitted over the convex pins 66 respectively, so as to position the springs 56. The spring 56 is lengthened by the recess hole 58, the elastic effect of the spring 56 on the screw block 52 is increased, and the reliability of effective screwing of the first screw thread structure 46 and the second screw thread structure 54 is enhanced.

Two lugs 14 laterally protrude from the cavity 10. Two embedding grooves 68 are formed inside the cover casing 60. The lugs 14 are embedded in the embedding grooves 68 respectively, so as to oppositely position the cavity 10 and the cover casing 60. When the operator controls the cover casing 60 and operates the plunger 40 to move linearly or rotate, the cavity 10 and the cover casing 60 are oppositely positioned, the cavity 10 will not perform rectilinear motion or rotation with the actuation of the piston 42, the operational reliability is enhanced.

We claim:

1. A fluid pressure gun device for balloon catheter, including a tubular cavity, a fluid tube, a pressure monitoring device, a plunger, a screw structure, a cover casing and a detent structure, wherein a chamber is formed inside the cavity for storing fluid, the front end of said cavity is connected to said fluid tube, said chamber communicates with said fluid tube, said fluid tube is provided with a connection fitting, so that the fluid tube communicates with a balloon catheter, said pressure monitoring device is disposed in the cavity for monitoring and indicating the pressure of the fluid, said plunger is movably disposed in said chamber, a piston is pivoted at the front end of said plunger, said piston and said cavity are fitted closely, so that said plunger pulls the piston to reciprocate in said chamber to inject the fluid into or extract the fluid from the balloon of said balloon catheter, an operating part is formed at the back end of said plunger, facilitating the axial displacement or rotation of said plunger, said screw structure is optionally combined with or disengaged from said plunger, so that said plunger resists the pressure from the fluid, and the displacement of said plunger and said piston is controlled;

said cover casing is arranged at the back end of the cavity, a chamber is formed inside the cover casing, said plunger protrudes out of the back end of the cover casing through said chamber, said plunger is provided with a first screw thread structure, said first screw thread structure is at least formed on opposite side of said plunger, said screw structure is disposed in said chamber, said screw structure comprises two screw blocks, said screw blocks are oppositely arranged centering on said plunger said screw blocks form a second screw thread structure fitting sad first screw thread structure respectively, so that said screw blocks are screwed on said plunger, said screw structure has several springs between said screw blocks and said cover casing, said springs prop said screw block and said cover casing respectively, so as to provide thrust, the screwing reliability of said screw blocks and said plunger is enhanced;

said detent structure comprises two cams, two arm levers and one connecting rod, wherein said cam is an elliptical disc, said cams are pivoted between said screw blocks respectively, and said cams are adjacent to both ends of said screw blocks far from said plunger respectively, a construction line is defined to pass through the center of said cams, the construction line radially passes through said plunger, said arm levers are connected to said cams respectively, both ends of said connecting rod are connected to said arm levers respectively, so that said arm levers pull said cams to rotate synchronously to perform combination or disengagement of said second screw thread structure and said first screw thread structure.

2. The fluid pressure gun device for balloon catheter defined in claim 1, wherein said screw blocks are oppositely movable in the chamber.

3. The fluid pressure gun device for balloon catheter defined in claim 1, wherein said cover casing forms two through grooves, said arm levers pass through the through grooves respectively, said arm levers are provided with a pivot respectively, said pivots are coaxial with said cams respectively, said pivots are pivoted on said cover casing respectively.

4. The fluid pressure gun device for balloon catheter defined in claim 1, wherein said connecting rod is adjacent to the rear edge of said cover casing, and a gripping part is formed in the midsection of said connecting rod, so as to enhance the handiness of turning said arm lever.

5. The fluid pressure gun device for balloon catheter defined in claim 1, wherein said connecting rod forms a notch fitting said plunger, said plunger passes through the notch.

6. The fluid pressure gun device for balloon catheter defined in claim 1, wherein said screw blocks form several recess holes respectively, several convex pins protrude from said cover casing, said springs are pivoted in said recess holes respectively, and said springs are fitted over said convex pins respectively, so as to position said springs.

7. The fluid pressure gun device for balloon catheter defined in claim 1, wherein said first screw thread structure surrounds the lateral circumference of said plunger.

8. The fluid pressure gun device for balloon catheter defined in claim 2, wherein said first screw thread structure surrounds the lateral circumference of said plunger.

9. The fluid pressure gun device for balloon catheter defined in claim 3, wherein said first screw thread structure surrounds the lateral circumference of said plunger.

10. The fluid pressure gun device for balloon catheter defined in claim 4, wherein said first screw thread structure surrounds the lateral circumference of said plunger.

11. The fluid pressure gun device for balloon catheter defined in claim 5, wherein said first screw thread structure surrounds the lateral circumference of said plunger.

12. The fluid pressure gun device for balloon catheter defined in claim 6, wherein said first screw thread structure surrounds the lateral circumference of said plunger.

13. The fluid pressure gun device for balloon catheter defined in claim 1, wherein two lugs laterally protrude from said cavity, two embedding grooves are formed inside said cover casing, said lugs are embedded in the embedding grooves respectively, so as to oppositely position said cavity and said cover casing.

14. The fluid pressure gun device for balloon catheter defined in claim 2, wherein two lugs laterally protrude from said cavity, two embedding grooves are formed inside said cover casing, said lugs are embedded in the embedding grooves respectively, so as to oppositely position said cavity and said cover casing.

15. The fluid pressure gun device for balloon catheter defined in claim 3, wherein two lugs laterally protrude from said cavity, two embedding grooves are formed inside said cover casing, said lugs are embedded in the embedding grooves respectively, so as to oppositely position said cavity and said cover casing.

16. The fluid pressure gun device for balloon catheter defined in claim 4, wherein two lugs laterally protrude from said cavity, two embedding grooves are formed inside said cover casing, said lugs are embedded in the embedding grooves respectively, so as to oppositely position said cavity and said cover casing.

17. The fluid pressure gun device for balloon catheter defined in claim 5, wherein two lugs laterally protrude from said cavity, two embedding grooves are formed inside said cover casing, said lugs are embedded in the embedding grooves respectively, so as to oppositely position said cavity and said cover casing.

18. The fluid pressure gun device for balloon catheter defined in claim 6, wherein two lugs laterally protrude from said cavity, two embedding grooves are formed inside said cover casing, said lugs are embedded in the embedding grooves respectively, so as to oppositely position said cavity and said cover casing.

\* \* \* \* \*